(12) United States Patent
Kanda

(10) Patent No.: US 10,145,713 B2
(45) Date of Patent: Dec. 4, 2018

(54) OPTICAL FIBER SENSOR DEVICE AND VIBRATION POSITION SPECIFYING METHOD

(71) Applicant: Oki Electric Industry Co., Ltd., Tokyo (JP)

(72) Inventor: Yoshihiro Kanda, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 32 days.

(21) Appl. No.: 15/640,677

(22) Filed: Jul. 3, 2017

(65) Prior Publication Data

US 2018/0058886 A1 Mar. 1, 2018

(30) Foreign Application Priority Data

Aug. 30, 2016 (JP) ................. 2016-168366

(51) Int. Cl.
*G01D 5/353* (2006.01)
*G01D 5/34* (2006.01)
*G01N 29/24* (2006.01)

(52) U.S. Cl.
CPC .............. *G01D 5/353* (2013.01); *G01D 5/344* (2013.01); *G01D 5/35351* (2013.01); *G01N 29/2418* (2013.01)

(58) Field of Classification Search
CPC .... G01D 5/353; G01D 5/344; G01D 5/35351; G01N 29/2418
See application file for complete search history.

(56) References Cited

U.S. PATENT DOCUMENTS

2003/0220749 A1\* 11/2003 Chen .................... A61B 5/0066
702/31

FOREIGN PATENT DOCUMENTS

JP 2000-040187 A 2/2000
JP 2008-203239 A 9/2008

OTHER PUBLICATIONS

Y. Kanda and H. Murai, "Novel extraction method of the maximum variation-rate of State-of-Polarization vector from time-varying birefringence", OFC2016, W2A.21.

(Continued)

*Primary Examiner* — Georgia Y Epps
*Assistant Examiner* — Don Williams
(74) *Attorney, Agent, or Firm* — Rabin & Berdo, P.C.

(57) ABSTRACT

The optical fiber sensor device comprises a probe light supply unit, an optical fiber sensor unit, and a polarization state measuring unit. The probe light supply unit generates and outputs a polarization switched light beam by alternately switching a polarized CW light beam in polarization directions orthogonal to each other with elapse of time. The optical fiber sensor unit includes a loop-state optical fiber into which the polarization switched light beam is input and which outputs a light wave reflecting a change of birefringence according to a stress applied from an outside in the polarization switched light beam. The polarization state measuring unit observes polarization states of the respective light waves propagating clockwise and counterclockwise through the optical fiber. The polarization state measuring unit calculates an angular velocity vector $\omega_b$ defined by an equation that specifies a relationship between a temporal change rate $ds_{out}(t)/dt$ of a Stokes vector $s_{out}(t)$ giving a polarization state of the light wave from the optical fiber and the Stokes vector $s_{out}(t)$ for each of the clockwise and counterclockwise light waves. The angular velocity vector $\omega_b$ gives a direction of a rotation center axis and a rotation angular velocity of the Stokes vector $s_{out}(t)$.

7 Claims, 4 Drawing Sheets

(56) References Cited

OTHER PUBLICATIONS

R. M. Jopson et al., "Measurement of Second-Order Polarization-Mode Dispersion Vectors in Optical Fibers", IEEE Photonics Technology Letters, vol. 11, No. 9, pp. 1153-1155, Sep. 1999.

* cited by examiner

OPTICAL FIBER SENSOR DEVICE AND VIBRATION POSITION SPECIFYING METHOD

CROSS REFERENCE TO RELATED APPLICATION(S)

This application is based upon and claims benefit of priority from Japanese Patent Application No. 2016-168366, filed on Aug. 30, 2016, the entire contents of which are incorporated herein by reference.

BACKGROUND

The present invention relates to an optical fiber sensor device and a vibration position specifying method.

When vibration is applied to an optical fiber from an outside, a polarization state of a light wave output from the optical fiber is temporally changed. A cause for that is a temporal change of birefringence of the optical fiber involved in the vibration (a variation both of the phase difference generated between the birefringent axis and of the birefringent axis), and as a result, a phenomenon of temporal change of the polarization state of the output light wave is observed. Using this phenomenon, by bonding the optical fiber to a fence or the like, inputting probe light to this optical fiber, and observing the temporal change of the polarization state of the output probe light, vibration of the fence or the like can be sensed. So far, as the optical fiber sensor device using this phenomenon of the temporal change of the polarization state of the output light wave, an intrusion detection optical fiber sensor and a rockfall sensing optical fiber sensor are disclosed in JP 2000-40187A (Patent Literature 1).

Moreover, a method of specifying a position of vibration applied to the optical fiber is disclosed in JP 2008-203239A (JP 5242098B; Patent Literature 2). This method is a fluctuation position detecting method in which the optical fiber is bonded in a loop state to an object to be measured such as a fence, polarized probe light is distributed to two parts, the distributed probe lights are led to both ends of the aforementioned loop-state optical fiber and made to propagate in different directions in this optical fiber, a temporal change of the polarization state of each of the output light waves is observed, and a vibration position is specified from a difference in start time of the change of their polarization states.

The light waves input into the optical fiber take time of approximately 5 ns to propagate for 1 m and thus, a difference is generated in the start time of the temporal change of the polarization states of clockwise and counterclockwise propagation lights by the position of vibration applied to the loop-state optical fiber, and the vibration position can be specified on the basis of this difference.

SUMMARY

In any of the aforementioned methods, stress fluctuation by vibration or the like is detected by a temporal change of the polarization state of the light wave output from the optical fiber. However, the temporal change of the polarization state of the output light wave depends both on a direction of an optic axis of birefringence of the optical fiber changed by the vibration and on the polarization state of the propagation light incident on a vibration point. In general, the polarization state of the light wave propagating through the optical fiber is at random, and the temporal change of birefringence of the optical fiber also depends on how the vibration of the optical fiber is applied.

Due to this dependence, an equal result cannot be obtained even for equal vibration only by observing the temporal change of the polarization state. Moreover, when the light wave is input so as to be coupled with the optic axis relating to birefringence of the optical fiber, the polarization state of the output light wave does not change. Therefore, a change of the birefringence of the optical fiber involved in vibration of the optical fiber cannot be grasped at all times only by observing the temporal change of the polarization state of the output light wave. This leads to overlooking of abnormal vibration which is a detection target or false detection.

Moreover, when the vibration position is specified by the fluctuation position detecting method disclosed in the aforementioned Patent Literature 2, in both the polarization state of the propagation light propagating clockwise through the loop-state optical fiber and the polarization state of the propagation light propagating counterclockwise, temporal changes of the polarization states of the both propagation lights are different; therefore, it is difficult in some cases to read out a difference in time when the temporal changes of the both polarization states are generated. That is, if a time waveform causing the temporal change of the polarization state is the same for the both, the time when the temporal change of the polarization state is generated can be easily made certain, but if the time waveforms of the both are different, it is difficult to specify the time when the temporal change of the polarization state is generated, and it becomes difficult to specify a fluctuation position of birefringence of the optical fiber.

Thus, an optical fiber sensor device and a vibration position specifying method using this device which can grasp a change of birefringence involved in vibration of the optical fiber without depending on the polarization state of propagation light propagating through the optical fiber are in demand.

An optical fiber sensor device according to an embodiment of the present invention includes: a probe light supply unit, an optical fiber sensor unit, and a polarization state measuring unit. The probe light supply unit generates and outputs a polarization switched light beam by alternately switching a polarized continuous wave light beam (CW light beam) in polarization directions orthogonal to each other with elapse of time. The optical fiber sensor unit includes a loop-state optical fiber into which the polarization switched light beam is input and which outputs a light wave reflecting a change of birefringence according to a stress applied locally from an outside in the polarization switched light beam.

The aforementioned polarization state measuring unit observes the polarization states of the respective light waves propagating clockwise and counterclockwise through the loop-state optical fiber to be output. Then, the aforementioned polarization state measuring unit calculates an angular velocity vector $\omega_b$ defined by the following equation (1) that specifies a relationship between a temporal change rate $ds_{out}(t)/dt$ of a Stokes vector $s_{out}(t)$ giving the polarization state of the light wave output from this loop-state optical fiber and this Stokes vector $s_{out}(t)$ for each of clockwise and counterclockwise light waves. The angular velocity vector $\omega_b$ gives a direction of a rotation center axis and a rotation angular velocity of the Stokes vector $s_{out}(t)$.

$$\frac{d}{dt}\vec{s}_{out}(t) = \vec{\omega}_b \times \vec{s}_{out}(t) \quad (1)$$

Further, the polarization state measuring unit specifies a fluctuation position of birefringence of the optical fiber from a difference in start time of a temporal change of an absolute value of the angular velocity vector $\omega_b$ with respect to each of the light waves propagating clockwise and counterclockwise through the loop-state optical fiber to be output.

Further, in a vibration position specifying method according to an embodiment of the present invention, in the aforementioned optical fiber sensor device, output of a polarization switched light beam, observation of the polarization state, and calculation of an angular velocity vector shown below are executed sequentially.

In the output of the polarization switched light beam described above, a polarization switched light beam is generated by alternately switching a polarized CW light beam in polarization directions orthogonal to each other with elapse of time and is output.

In the observation of the polarization state described above, the polarization switched light beam is branched into two parts and the two parts are made to propagate clockwise and counterclockwise through the loop-state optical fiber, and the polarization states of the respective light waves output from this loop-state optical fiber are observed.

In the calculation of the angular velocity vector, calculated is the angular velocity vector $\omega_b$ defined by the aforementioned equation (1) that specifies the relationship between a temporal change rate $ds_{out}(t)/dt$ of the Stokes vector $s_{out}(t)$ giving the polarization states of the respective light waves output from the optical fiber and this Stokes vector $s_{out}(t)$.

The vibration position specifying method preferably further includes specification of a birefringence fluctuation position. In specification of the birefringence fluctuation position, a fluctuation position of the birefringence of the optical fiber is specified from the difference in start time of the temporal change of an absolute value of this angular velocity vector $\omega_b$ with respect to the respective light waves propagating clockwise and counterclockwise through the loop-state optical fiber to be output.

The temporal change of the absolute value of this angular velocity vector $\omega_b$ does not depend on the polarization state of the light wave input to a vibration generation spot but expresses a specific state relating to the temporal change of birefringence of the optical fiber. Thus, the specific state of birefringence of the optical fiber can be detected with good reproducibility, and the temporal changes of both the polarization state of the light wave propagating clockwise through the loop-state optical fiber to be output and the polarization state of the light wave propagating counterclockwise to be output are equal. The angular velocity vector $\omega_b$ is a specific state relating to temporal change characteristics of birefringence of the optical fiber. That is, since the angular velocity vector $\omega_b$ is a nature of the optical fiber itself, it does not depend on the polarization state of an incident light. Thus, it does not depend on the random incident polarization state like the prior-art temporal change rate of the polarization state, and a cause of a change of the polarized wave state itself can be quantified. Since this nature is a characteristic of the optical fiber itself, an equal result is obtained whether it is acquired from clockwise light or from counterclockwise light.

Therefore, by comparing the time when the absolute value of the angular velocity vector acquired from the light wave propagating clockwise through the loop-state optical fiber to be output is changed with the time when the absolute value of the angular velocity vector acquired from the light wave propagating counterclockwise to be output is changed, a fluctuation position of birefringence of the optical fiber can be specified.

DETAILED DESCRIPTION OF THE EMBODIMENT(S)

Figure 1:
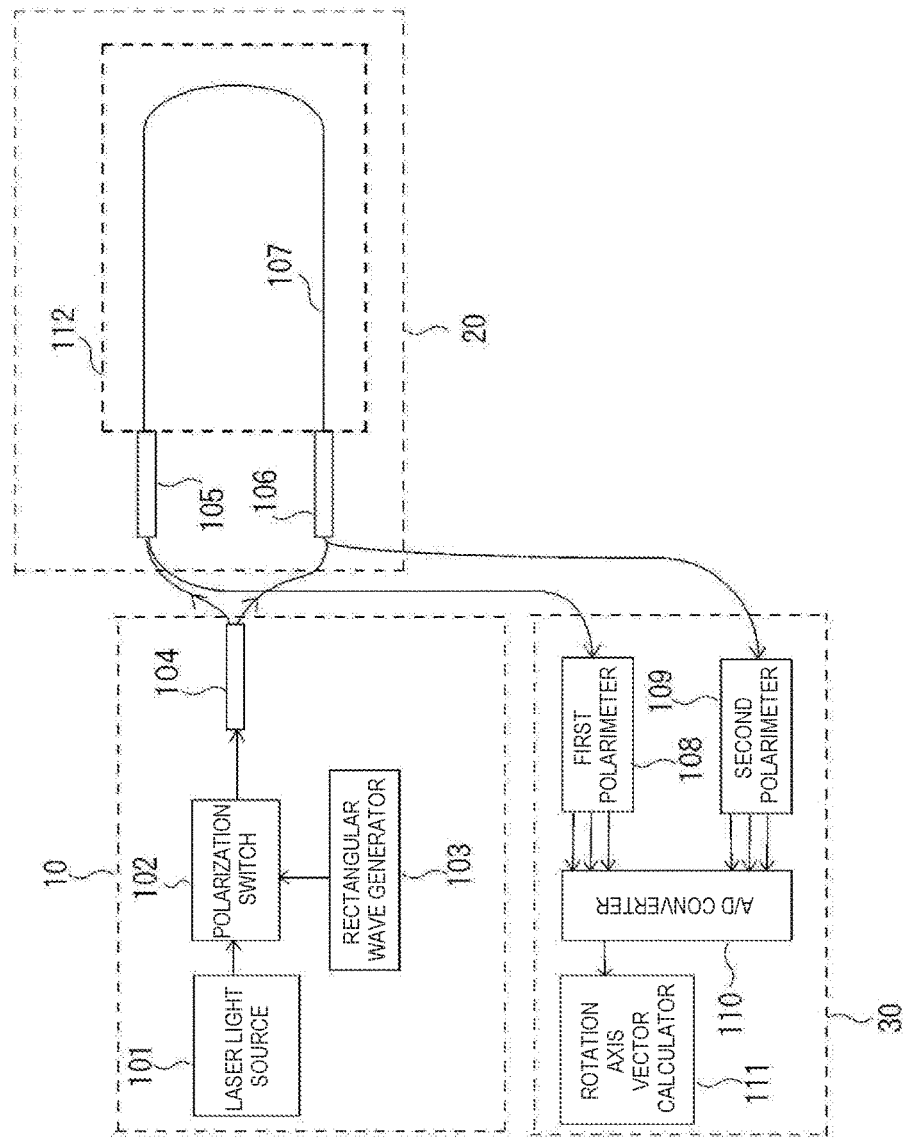
FIG. 1 is a block configuration view illustrating a schematic configuration of an optical fiber sensor device according to an embodiment of the present invention.

Hereinafter, referring to the appended drawings, preferred embodiments of the present invention will be described in detail. It should be noted that, in this specification and the appended drawings, structural elements that have substantially the same function and structure are denoted with the same reference numerals, and repeated explanation thereof is omitted.

An embodiment of this invention will be described below by referring to the drawings. Note that FIG. 1 illustrates a configuration example of an optical fiber sensor device according to an embodiment of the present invention. It only schematically illustrates an arrangement relationship among constituent elements so that the embodiment of the present invention can be understood and does not limit the present invention to the illustrated example. Moreover, in the description below, specific elements, operation conditions and the like may be taken up but these elements and operation conditions are ones of suitable examples, and the present invention is not limited by them. Moreover, a vector quantity is handled in the explanation of this specification, but rightward arrows given above characters expressing the vector quantity may be omitted within a range not causing confusion in some cases.

<Optical Fiber Sensor Device>

By referring to FIG. 1, the optical fiber sensor device according to the embodiment of the present invention will be described. This optical fiber sensor device includes a probe light supply unit 10, an optical fiber sensor unit 20, and a polarization state measuring unit 30.

The probe light supply unit 10 generates a polarization switched light beam by alternately switching an arbitrary polarized CW light beam fixed with respect to time in polarization directions orthogonal to each other with elapse of time and outputs it. The optical fiber sensor unit 20 includes a loop-state optical fiber 107 into which this polarization switched light beam is input and which outputs a light wave in the polarization state reflecting a change in the polarization state of the input light wave in accordance with the change of birefringence according to a stress applied locally from an outside. The polarization state measuring unit 30 observes the polarization states of the respective light waves propagating clockwise and counter-clockwise through the loop-state optical fiber 107 to be output.

The probe light supply unit 10 includes a laser light source 101, a polarization switch 102, a rectangular wave generator 103, and an optical branching device 104.

The optical fiber sensor unit 20 includes a first optical circulator 105, a second optical circulator 106, and the loop-state optical fiber 107. The loop-state optical fiber 107 is fixed by bonding to a target 112 to be measured such as a fence. When vibration is applied to this target 112 to be measured, a part of the loop-state optical fiber 107 is vibrated in conjunction with this vibration. By means of this vibration, the state of birefringence of a vibrated portion of the loop-state optical fiber 107 is changed.

The polarization state measuring unit 30 includes a first polarimeter 108, a second polarimeter 109, an analog-digital (A/D) converter 110, and an angular velocity vector calculator 111.

The laser light source 101 outputs the CW light beam, the rectangular wave generator 103 supplies a rectangular wave electric signal to the polarization switch 102, this polarization switch 102 outputs a polarization switched light beam in synchronization with the rectangular wave electric signal, and the optical branching device 104 branches the polarization switched light beam to two parts and supplies them to the first optical circulator 105 and the second optical circulator 106.

Since the rectangular wave electric signal output from the rectangular wave generator 103 is applied to the polarization switch 102, the polarization state of the CW light beam output from the laser light source 101 is input into the polarization switch 102 and then, alternately switched to the polarization states in which the polarization directions are orthogonal to each other in a time cycle of this rectangular wave electric signal. As a result, the polarization switched light beam in which the polarization state of the CW light beam is alternately switched to the two polarization states orthogonal to each other with elapse of time is output from the polarization switch 102.

A switching cycle for alternately switching the two orthogonal polarization states of the polarization switch 102 is set sufficiently smaller than time required for polarization fluctuation expected for the loop-state optical fiber 107.

The electric signal output from the rectangular wave generator 103 is preferably a rectangular wave but is not limited to the rectangular wave as long as it is an electric signal which is supplied to the polarization switch 102, output from the polarization switch 102, and enables alternate switching to the 2 polarization states orthogonal to each other at a time interval half of the time cycle of the electric signal with elapse of time.

The polarization switch 102 preferably uses a polarized wave modulator using lithium niobate, for example, but any device can be used as long as it can alternately switch the polarization state to the two polarization states orthogonal to each other with elapse of time. For example, a polarized wave rotator using an electro-optical effect, a polarized wave rotator using a magneto-optical effect or a ½ wavelength plate of a mechanical driving type can be also used.

One of the polarization switched light beams having been branched to two parts is input so as to propagate clockwise through the loop-state optical fiber 107, while the other is input so as to propagate counterclockwise, through the first and second optical circulators (105, 106).

The light wave output propagating clockwise through the loop-state optical fiber 107 is input into the second polarimeter 109 through the second optical circulator 106, and a Stokes parameter of this light wave is observed. On the other hand, the light wave propagating counterclockwise through the loop-state optical fiber 107 to be output is input into the first polarimeter 108 through the first optical circulator 105, and the Stokes parameter of this light wave is observed.

The Stokes parameter of each of the light waves observed by the first and second polarimeters (108, 109) is converted into a digital signal in the A/D converter 110 and input into the angular velocity vector calculator 111. The angular velocity vector calculator 111 calculates the angular velocity vector $\omega_b$ for each of the light waves propagating clockwise and counterclockwise through the loop-state optical fiber 107, from the Stokes parameters observed by the first and second polarimeters (108, 109).

Each of the first and second polarimeters (108, 109) may be any device as long as it can observe time dependence of the Stokes parameter, and its measurement speed band only needs to satisfy sampling theorem with respect to a polarization fluctuation speed of time dependency of the Stokes vector of the loop-state optical fiber 107.

As the angular velocity vector calculator 111, a commercial personal computer (PC) in which software for calculating angular velocity vector $\omega_b$ from time dependency of the Stokes parameter of the polarization switched light beam is installed can be used.

<Angular Velocity Vector>

In explaining an operation principle of the optical fiber sensor device, an angular velocity vector $\omega_b$ which is a required basic concept will be described.

The time development of the polarization state of the light wave output from the optical fiber is given by the following equation (1) according to Y. Kanda and H. Murai, "Novel extraction method of the maximum variation-rate of State-of-Polarization vector from time-varying birefringence," OFC2016, W2A.21 (Non-Patent Literature 1).

$$\frac{d}{dt}\vec{s}_{out}(t) = \vec{\omega}_b \times \vec{s}_{out}(t) \tag{1}$$

Here, $s_{out}(t)$ is a Stocks vector of three rows by one column expressing the polarization sate of the light wave output from this optical fiber at time t with respect to an arbitrary light wave input into the optical fiber. Here, "t" is time defined at an output end of the optical fiber.

The angular velocity vector $\omega_b$ is a characteristic specific to the optical fiber reflecting the temporal change of birefringence and is a real vector of three rows by one column giving rotation around a direction of the angular velocity vector $\omega_b$ to the Stokes vector $s_{out}(t)$ in a micro time width dt. On the other hand, the polarization state $s_{out}(t)$ of the light wave output from the optical fiber depends on the polarization state of the light wave input into the optical fiber, and a head of the Stokes vector expressing this polarization state can pass any point on the Poincare sphere surface.

An important point here is that the angular velocity vector $\omega_b$ indicates a temporal change of birefringence specific to the optical fiber and does not depend on the polarization state of the input light wave. That is, the polarization state $s_{out}(t)$ of the light wave output from the optical fiber depends on the polarization state of the light wave input into the optical fiber, while the angular velocity vector $\omega_b$ does not depend on the polarization state of the input light wave and thus, the temporal change of birefringence specific to the optical fiber can be known by measuring the angular velocity vector $\omega_b$ without depending on the polarization state of the input light wave.

In general, the polarization state of the propagation light propagating through the optical fiber is different depending on a passage spot of the optical fiber. Thus, the polarization state of the clockwise propagation light is different from the polarization state of the counterclockwise propagation light at a vibration generation spot in the loop-state optical fiber 107. However, since a specific state of birefringence of the optical fiber given by the angular velocity vector $\omega_b$ is a characteristic specific to the optical fiber, even if stress fluctuation by vibration or the like occurs in the loop-state optical fiber 107 used in the embodiment of the present invention, the angular velocity vectors $\omega_b$ calculated from the respective light waves propagating clockwise and counterclockwise through the loop-state optical fiber 107 to be output have equal temporal change characteristics. However, if stress fluctuation occurs due to vibration or the like in the loop-state optical fiber 107, a difference is generated in start time of the temporal change in the angular velocity vectors $\omega_b$ calculated from the respective light waves propagating clockwise and counterclockwise to be output depending on the fluctuation position of birefringence of the loop-state optical fiber 107. The fluctuation position of birefringence in the loop-state optical fiber 107 is specified from the start time difference in the temporal change.

The angular velocity vector $\omega_b$ is acquired by measuring a rotation matrix R(t) of 3 rows by 3 columns expressing birefringence of the loop-state optical fiber 107. Here, at time t when the light wave is output from the loop-state optical fiber 107, it is assumed that the Stokes vector of the light wave input into this loop-state optical fiber 107 is $s_{in}(t)$ and the Stokes vector of the output light wave is $s_{out}(t)$. Moreover, it is assumed, here, that the polarization state of the light wave input into the loop-state optical fiber 107 does not fluctuate.

A relationship between the Stokes vectors $s_{in}(t)$ and $s_{out}(t)$ is given by the following equation (2) by using the rotation matrix R(t).

$$\vec{s}_{out}(t) = R(t)\vec{s}_{in} \tag{2}$$

A primary time differential coefficient of the equation (2) is given by the following equation (3).

$$\frac{d}{dt}\vec{s}_{out}(t) = \left\{\frac{d}{dt}R(t)\right\}\vec{s}_{in} \tag{3}$$

From the equation (2) and the equation (3), the following equation (4) is obtained.

$$\vec{s}_{in}(t) = R^\dagger(t)\vec{s}_{out} \tag{4}$$

Here, "†" means an adjoint operator. By substituting the equation (4) to the right side of the equation (3), the following equation (5) is obtained.

$$\frac{d}{dt}\vec{s}_{out}(t) = \left\{\frac{d}{dt}R(t)\right\}R^\dagger(t)\vec{s}_{out} \tag{5}$$

By comparing the equation (1) and the equation (5), an angular velocity vector product operator expression "$\omega_b \times$" is given by the following equation (6).

$$\vec{\omega}_b \times = \left\{\frac{d}{dt}R(t)\right\}R^\dagger(t) \tag{6}$$

Moreover, by expressing the angular velocity vector product operator expression "$\omega_b \times$" in a matrix, it is given by the following equation (7).

$$\vec{\omega}_b \times = \begin{bmatrix} 0 & -\omega_{b3} & \omega_{b2} \\ \omega_{b3} & 0 & -\omega_{b1} \\ -\omega_{b2} & \omega_{b1} & 0 \end{bmatrix} \tag{7}$$

Here, the angular velocity vector $\omega_b$ is a column vector of 3 rows and 1 column and is expressed by the following equation (8).

$$\vec{\omega}_b = \begin{bmatrix} \omega_{b1} \\ \omega_{b2} \\ \omega_{b3} \end{bmatrix} \tag{8}$$

<Measurement of Angular Velocity Vector>

As described above, by measuring the temporal change of the rotation matrix R(t), the angular velocity vector $\omega_b$ is acquired from the equation (6) and the equation (7). Moreover, an absolute value $|\omega_b|$ giving a magnitude of the angular velocity vector $\omega_b$ matches an angular velocity (rad/s) of a circle drawn on the Poincare sphere surface by the head of the Stokes vector $s_{out}(t)$ of the output light wave with elapse of time.

Since a position of the head of the Stokes vector $s_{out}(t)$ of the output light wave is different depending on the polarization state of the light wave input into the optical fiber, a radius of the circle of $s_{out}(t)$ drawn on the Poincare sphere also depends on the polarization state of the input light wave. However, the angular velocity of the circle drawn by the head of $s_{out}(t)$ does not depend on the polarization state of the input light wave regardless of the radius of the circle. As described above, by measuring the angular velocity vector $\omega_b$ giving the specific state of birefringence in the optical fiber itself, the temporal change of birefringence of the optical fiber can be quantified without depending on the polarization state of the input light wave.

Measurement of the rotation matrix R(t) at the time t when the light wave is output from the optical fiber can be acquired from the polarization state of the light wave measured for each of the two polarization states orthogonal to each other. However, there is one polarization state that can be defined instantaneously to the rotation matrix R(t) which temporally changes. However, by switching the polarization state of the input light wave to two polarization states and by separating the polarization state of the output light wave into two in a switching cycle in a short time interval of such a degree that the rotation matrix R(t) can be considered as steady, it can be considered that the polarization state of the light wave can be measured substantially simultaneously for the two polarization states orthogonal to each other.

As described above, by setting the switching cycle for alternately switching the two orthogonal polarization states of the polarization switch 102 sufficiently smaller than time required for polarization fluctuation expected for the loop-state optical fiber 107, the polarization state of the light wave output from the loop-state optical fiber 107 is measured substantially at the same time t for the two polarization states orthogonal to each other, and it can be considered that the rotation matrix R(t) is acquired.

Here, by referring to FIG. 1, an operating method of the optical fiber sensor device according to the embodiment of the present invention will be specifically described in measurement of the angular velocity vector $\omega_b$.

When the laser light source 101 is driven and the rectangular wave generator 103 is driven, the polarization switched light beam is output from the polarization switch 102. Here, a peak-to-peak voltage ($V_{pp}$) of the rectangular wave electric signal supplied from the rectangular wave generator 103 to the polarization switch 102 is set to a half ($V_{pp}=V_\pi/2$) of an applied voltage $V_\pi$ at which a phase difference between orthogonal polarization axes of the light wave output from the polarization switch 102 becomes $\pi$. That is, by supplying the rectangular wave electric signal satisfying this condition to drive the polarization switch 102, the light wave output from the polarization switch 102 becomes the polarization switched light beam which is alternately switched to the orthogonal polarization states for every half the time cycle of the rectangular wave electric signal.

A frequency of the rectangular wave electric signal supplied by the rectangular wave generator 103 to the polarization switch 102 is preferably twice or more of the temporal change rate of the polarization state of the light wave output from the loop-state optical fiber 107. Here, the temporal change rate of the polarization state is a physical quantity expressed, with respect to the polarization state $s_{out}(t)$ of the output light wave, by an absolute value of its time differential $ds_{out}(t)/dt$.

The polarization switched light beam output from the polarization switch 102 is branched to two parts in the optical branching device 104, one of which propagates clockwise through the loop-state optical fiber 107 to be input into the second polarimeter 109 through the second optical circulator 106, while the other propagates counterclockwise through the loop-state optical fiber 107 to be input into the first polarimeter 108 through the first optical circulator 105. Outputs from the first and second polarimeters (108, 109) are converted into digital signals by the A/D converter 110 and then, input into the angular velocity vector calculator 111.

Here, a sampling frequency of the A/D converter 110 only needs to be a frequency satisfying sampling theorem with respect to the rectangular wave electric signal generated in the rectangular wave generator 103. The sampling theorem is a theorem quantitatively indicating an interval at which sampling should be performed when an analog signal is to be converted into a digital signal. For example, assuming that the frequency of the rectangular wave electric signal generated in the rectangular wave generator 103 is 100 Hz, by using the A/D converter of approximately 1 kS/s which is 10 times thereof, a rectangular waveform can be sufficiently reproduced. Here, kS/s means the number of sampling points obtained per second.

<Verification by Experiment>

By referring to FIGS. 2A to 2D, a result of experiment in which vibration is applied to any of spots on the loop-state optical fiber 107, each of the temporal changes of the Stokes parameters ($S_1$, $S_2$, $S_3$) observed by the second polarimeter 109 is converted into a digital signal by the A/D converter 110 and then, it is input into the angular velocity vector calculator 111 and observed will be described.

Here, the frequency of the rectangular wave electric signal generated in the rectangular wave generator 103 was set to 100 Hz, and the sampling frequency of the A/D converter 110 was set to 1.22 kHz. Moreover, in FIGS. 2A to 2D, a horizontal axis indicates time by the unit of ms and a vertical axis indicates a magnitude of the Stokes parameter.

Figure 2A:
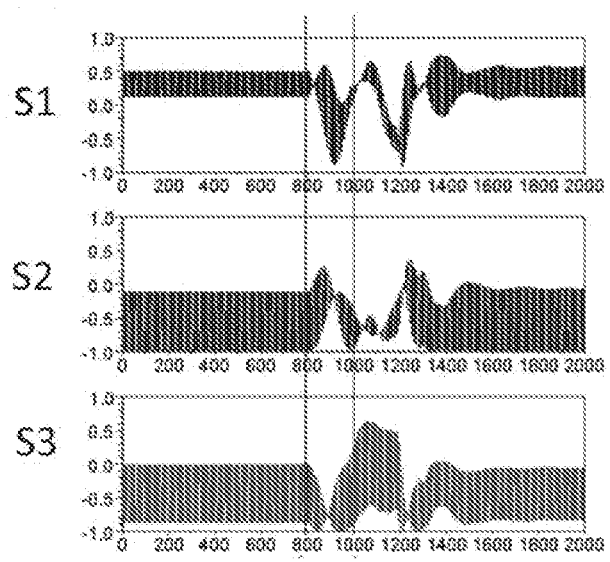
FIG. 2A is a view illustrating a temporal change of a polarization state of a light wave propagating clockwise through a loop-state optical fiber to be output and is a graph illustrating a change of a Stokes parameter to time.
Figure 2B:
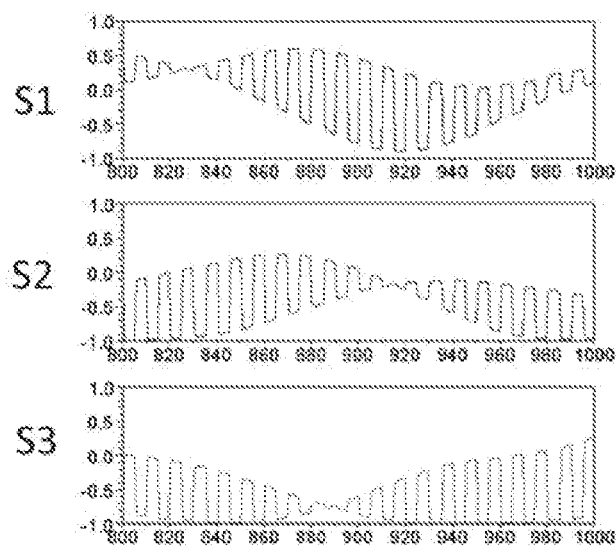
FIG. 2B is a view illustrating the temporal change of the polarization state of the light wave propagating clockwise through the loop-state optical fiber to be output and is a graph illustrating a change of the Stokes parameter in a range of 800 to 1000 ms in an enlarged manner.

FIG. 2A is a view illustrating a temporal change of the polarization state of the light wave propagating clockwise through the loop-state optical fiber 107 to be output, and FIG. 2B is a graph illustrating a change of the Stokes parameter in a range of 800 to 1000 ms in an enlarged manner. As illustrated in FIGS. 2A and 2B, the Stokes parameter observed by the second polarimeter 109 is switched at a half of the time cycle (10 ms in the case where the frequency of the rectangular wave is 100 Hz) of the rectangular wave electric signal generated in the rectangular wave generator 103. By taking out the Stokes parameter in correspondence to a half cycle of the rectangular wave electric signal generated in the rectangular wave generator 103, the Stokes parameter can be separated for every two polarization components orthogonal to each other.

Figure 2C:
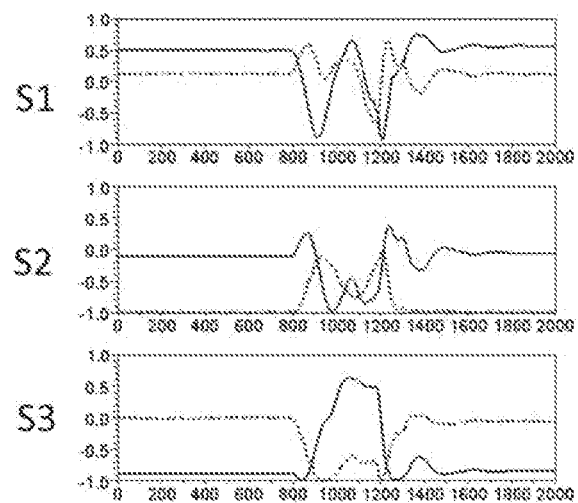
FIG. 2C is a view illustrating the temporal change of the polarization state of the light wave propagating clockwise through the loop-state optical fiber to be output and is a graph illustrating the Stokes parameter separated for every 2 polarization components orthogonal to each other.

In FIG. 2C, the Stokes parameter is separated for every two polarization components orthogonal to each other at each half cycle of the rectangular wave electric signal, and a Stokes vector $t_1$ which is one of the components is indicated by a solid line, while a Stokes vector $t_a$ which is the other component by a broken line.

Figure 2D:
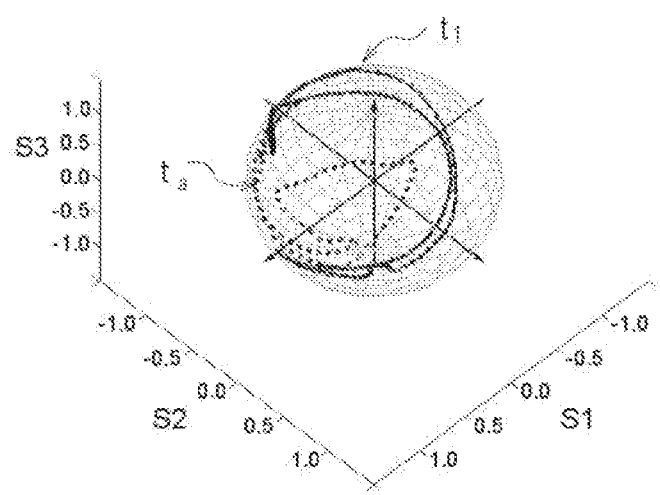
FIG. 2D is a view illustrating the temporal change of the polarization state of the light wave propagating clockwise through the loop-state optical fiber to be output and is a view illustrating trajectories of the temporal changes of heads of Stokes vectors $t_1$ and $t_a$ expressing the 2 polarization states orthogonal to each other on a Poincare sphere.

FIG. 2D is a view illustrating trajectories of the temporal changes of heads of the Stokes vectors $t_1$ and $t_a$ indicating the two polarization states orthogonal to each other on the Poincare sphere. In FIG. 2D, a trajectory of the Stokes vector $t_1$ is indicated by a solid line and a trajectory of the Stokes vector $t_a$ is indicated by a broken line.

Here, each of the Stokes vectors $t_1$ and $t_a$ is noted in vector components as indicated in the following equations (9a) and (9b):

$$t_1 = (t_{11},\ t_{12},\ t_{13})^T \tag{9a}$$

$$t_a = (t_{a1},\ t_{a2},\ t_{a3})^T \tag{9b}$$

and new two vectors $t_2$ and $t_3$ are defined to be indicated by the following equations (10a) and (10b), respectively:

$$t_2 = t_3 \times t_1 = (t_{21},\ t_{22},\ t_{23})^T \tag{10a}$$

$$t_3 = t_1 \times t_a = (t_{31},\ t_{32},\ t_{33})^T \tag{10b}$$

where the Stokes vectors $t_1$, $t_a$, $t_2$, and $t_3$ are all standardized so that their absolute values are 1.

According to R. M. Jopson, L. E. Nelson, and H. Kogelnik, "Measurement of Second-Order Polarization-Mode Dispersion Vectors in Optical Fibers," IEEE Photonics Technology Letters, vol. 11, No. 9, (1999), pp. 1153-1155 (Non-Patent Literature 2), the rotation matrix R(t) can be expressed as the following equations (11) and (12) by using the vector $t_1$, the vector $t_2$, and the vector $t_3$.

$$R^\dagger = \begin{bmatrix} t_{11} & t_{12} & t_{13} \\ t_{21} & t_{22} & t_{23} \\ t_{31} & t_{32} & t_{33} \end{bmatrix} \quad (11)$$

$$R = \begin{bmatrix} t_{11} & t_{21} & t_{31} \\ t_{12} & t_{22} & t_{32} \\ t_{13} & t_{23} & t_{33} \end{bmatrix} \quad (12)$$

The rotation matrix R(t) is a Mueller matrix, and the Mueller matrix is generally a matrix of 4 rows and 4 columns but here, and it is treated as a matrix of remaining 3 rows and 3 columns by excluding a component on a first row and a component on a first column By acquiring this rotation matrix R(t) from the temporal changes of the Stokes vectors $t_1$ and $t_a$, the temporal change of the angular velocity vector $\omega_b$ to elapse of time can be acquired by the aforementioned equation (6) and equation (7).

The method of acquiring the angular velocity vector $\omega_b$ from the light wave propagating clockwise through the loop-state optical fiber 107 to be output has been described above, but the angular velocity vector $\omega_b$ can be acquired similarly from the light wave propagating counterclockwise to be output. An important point, here, is that the rotation matrix R(t) indicating birefringence of the loop-state optical fiber 107 does not depend on clockwise or counterclockwise but is equal, and the temporal change of the angular velocity vector $\omega_b$ acquired from the rotation matrix R(t) is equal in principle regardless of clockwise or counterclockwise.

Figure 3:
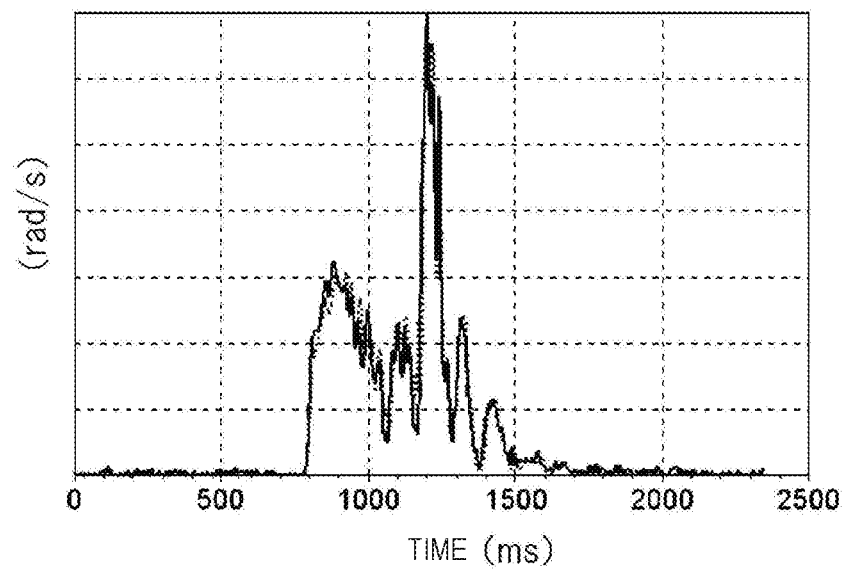
FIG. 3 is a graph illustrating the temporal change of an absolute value of an angular velocity vector $\omega_b$ obtained from observation of each of the light waves propagating clockwise and counterclockwise to be output.

By referring to FIG. 3, an example of the temporal change of the absolute value of the angular velocity vector $\omega_b$ acquired from each of the light waves propagating clockwise and counterclockwise to be output by applying vibration to the loop-state optical fiber 107 will be described. The horizontal axis in FIG. 3 indicates time by the unit of ms and the vertical axis indicates an absolute value $|\omega_b|$ (rad/s) of the angular velocity vector by an arbitrary scale. In FIG. 3, the temporal changes of the absolute values of the angular velocity vectors obtained from the light waves propagating clockwise and counterclockwise to be output are indicated by a solid line for the clockwise and a broken line for the counterclockwise.

As illustrated in FIG. 3, it is known that curves giving the temporal changes of the absolute values of the angular velocity vectors acquired from the light waves propagating clockwise and counterclockwise to be output are substantially overlapped with each other and are the same.

A position where the vibration of the loop-state optical fiber 107 is applied is specified by comparing the vibration start time from the temporal changes of the absolute values of the angular velocity vectors acquired from the light waves propagating clockwise and counterclockwise to be output. For example, when a whole length of the loop-state optical fiber 107 is 1 km, if change start time meaning vibration of the curve giving the temporal change of the absolute value of the angular velocity vector corresponding to each of clockwise and counterclockwise is equal, it is considered that, after propagation light propagating through the loop-state optical fiber 107 is subjected to an influence of the vibration, it propagates for the same distance for the clockwise and the counterclockwise and output, and it can be interpreted that the vibration occurred at a middle position of the loop-state optical fiber 107.

On the other hand, a case where, assuming that a 0 m point of the loop-state optical fiber 107 is a connection point between the first optical circulator 105 and the loop-state optical fiber 107, and a 1 km point is a connection point between the second optical circulator 106 and the loop-state optical fiber 107, vibration is applied at 250 m point, is taken up as an example. In this case, since it takes 5 ns for the propagation light to propagate for 1 m through the loop-state optical fiber 107, the start time of the temporal change of the absolute value of the angular velocity vector corresponding to counterclockwise is earlier by 2.5 µs than the start time corresponding to clockwise. That is, the vibration occurrence point can be specified from a difference in the start time of the temporal changes of the absolute values of the angular velocity vectors corresponding to clockwise and counterclockwise.

This uses the fact that a state of the temporal change of the angular velocity vector which is a nature of the optical fiber itself is equal whether it is acquired from the clockwise propagation light or from the counterclockwise propagation light. That is, the fluctuation position of the birefringence of the optical fiber can be specified from the difference in the vibration start time of waveforms expressing the temporal changes of the magnitudes of the equal angular velocity vectors acquired from the both.

<Vibration Position Specifying Method>

In order to specify a birefringence fluctuation position by the optical fiber sensor device illustrated in FIG. 1, the following four steps are executed.

Polarization Switched Light Beam Output Step:

The CW light beam output from the laser light source 101 is input into the polarization switch 102 and is synchronized with the rectangular wave electric signal, and the polarization state of the CW light beam is alternately switched to two polarization states orthogonal to each other with elapse of time and the polarization switched light beam is output from the polarization switch 102.

Polarization State Observation Step:

The polarization switched light beam is branched into two parts by the optical branching device 104 and the polarization states of respective light waves propagating clockwise and counterclockwise through the loop-state optical fiber 107 to be output from the loop-state optical fiber 107 are observed by the first and second polarimeters (108, 109) included in the polarization sate measuring unit 30. Here, what is observed is the Stokes parameters ($S_1$, $S_2$, $S_3$).

Angular Velocity Vector Calculation Step:

From the temporal change of the polarization state of each of the light waves propagating clockwise and counterclockwise through the loop-state optical fiber 107 to be output, the angular velocity vector $\omega_b$ is calculated. The angular velocity vector $\omega_b$ is calculated by the angular velocity vector calculator 111 included in the polarization state measuring unit 30. Here, assuming that the angular velocity vector $\omega_b$ is $(\omega_{b1}, \omega_{b2}, \omega_{b3})^T$ as shown in the aforementioned equation (8), the angular velocity vector product operator expression "$\omega_b \times$" is given by the aforementioned equation (7).

Birefringence Fluctuation Position Specifying Step:

The birefringence fluctuation position of the optical fiber is specified from the difference in the start time of the temporal change of the absolute value of the angular velocity vector $\omega_b$ to each of the light waves propagating clockwise and counterclockwise through the loop-state optical fiber 107 to be output.

As the birefringence fluctuation position specifying step of the specifying method of the birefringence fluctuation position, those other than the aforementioned birefringence fluctuation position specifying step can be considered. For example, the loop-state optical fiber 107 is observed only in one direction of clockwise or counterclockwise and instead, the polarization switched light beam is input in a pulse state at a certain interval intermittently, and the difference between time of input into the loop-state optical fiber 107 and time when the polarization state of the output light wave is changed is calculated so that the position can be also specified. That is, what is important is that the angular velocity vector $\omega_b$ can be acquired. If the angular velocity vector $\omega_b$ can be acquired, the birefringence fluctuation position can be made certain without depending on the polarization state of the propagation light propagating through the loop-state optical fiber 107 even if the step other than the aforementioned birefringence fluctuation position specifying step is used.

<Advantages>

As having been described, both in the intrusion detection device disclosed in Patent Literature 1 and the fluctuation position detecting method by the optical fiber sensor disclosed in Patent Literature 2, probing of vibration or the like is made on the basis of the temporal change of the Stokes vector $s_{out}(t)$ giving the polarization states of the respective light waves output from the optical fiber. However, the temporal change of the Stokes vector $s_{out}(t)$ depends in principle on the polarization state of the probe light passing through a spot which should be detected. Thus, the detecting method by detecting the temporal change of the Stokes vector $s_{out}(t)$ is poor in reproducibility.

Moreover, in the method employed in the fluctuation position detecting method by the optical fiber sensor disclosed in Patent Literature 2, the fluctuation position is specified from the occurrence time difference of the temporal change of the Stokes vector $s_{out}(t)$ of each of the probe lights propagating in directions opposite to each other in the loop-state optical fiber.

However, as will be described below by referring to FIG. 4, the temporal changes of the Stokes vector $s_{out}(t)$ of the respective probe lights propagating in directions opposite to each other in the loop-state optical fiber are different from each other. Thus, to specify a time change spot reflecting a change in the birefringence occurring in the loop-state optical fiber by comparing the different temporal change curves involves difficulty. This point will be specifically described below.

Figure 4:
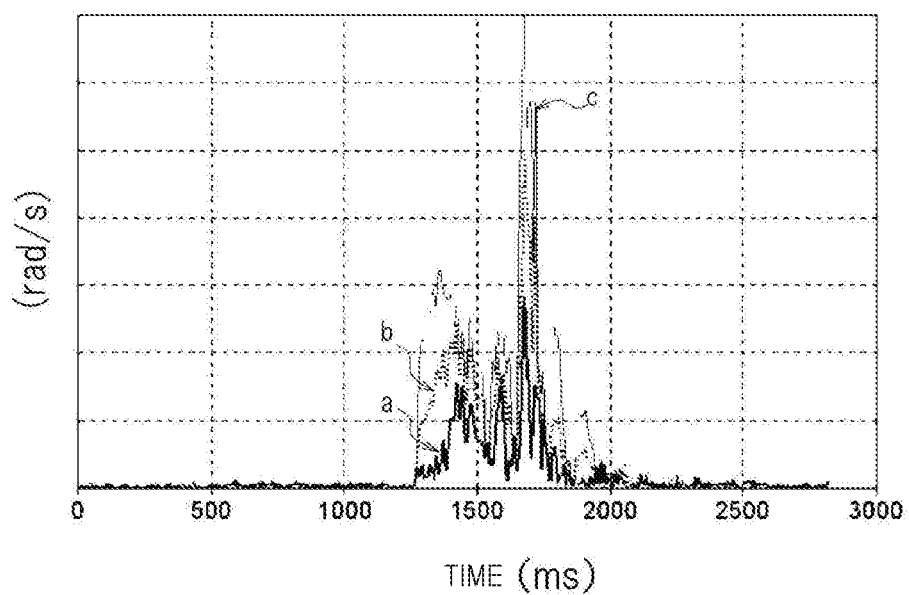
FIG. 4 is a graph illustrating a temporal change of a magnitude of a temporal change rate of the Stokes vector expressing the polarization states of the light waves propagating clockwise and counterclockwise to be output and a temporal change of the absolute value of the angular velocity vector of the light wave propagating clockwise.

FIG. 4 illustrates a temporal change of the magnitude of the temporal change rate $ds_{out}(t)/dt$ of the Stokes vector $s_{out}(t)$ expressing the polarization state of the light wave output after clockwise and counterclockwise propagation through the loop-state optical fiber 107. The horizontal axis indicates time by the unit of millisecond (ms) and the vertical axis indicates a magnitude of the temporal change rate $ds_{out}(t)/dt$ of the Stokes vector expressing the polarization state of the light wave output after clockwise and counterclockwise propagation and a temporal change of the absolute value $|\omega_b|$ (rad/s) of the angular velocity vector obtained from the light wave propagating clockwise to be output. A bold solid line a indicates a magnitude of the temporal change rate of the Stokes vector of the light wave propagating clockwise to be output, while a broken line b indicates a magnitude of the temporal change rate of the Stokes vector of the light wave propagating counterclockwise. Moreover, for comparison, the temporal change of the absolute value of the angular velocity vector of the light wave propagating clockwise is indicated by a thin solid line c.

As is obvious from comparison between the bold solid line a and the broken line b, curves giving the temporal changes of the magnitudes of the temporal change rates of the Stokes vectors expressing the polarization states of the clockwise light wave and the counterclockwise light wave are largely different. Thus, it is obvious that specification of the temporal change spot reflecting a change of birefringence locally occurring in the loop-state optical fiber is difficult by comparing the bold solid line a and the broken line b.

Moreover, in the method of detecting stress fluctuation by vibration or the like by a temporal change of a magnitude of the temporal change rate of the Stokes vector expressing the polarization state of the light wave output from the loop-state optical fiber, when the light wave happening to be input is input in a polarization state coupling to an optic axis relating to birefringence of the optical fiber, there is a problem that the polarization state of the output light wave does not temporally change. In this case, even if a change in the birefringence involved in the vibration occurs, no change appears in a curve giving a temporal change of a magnitude of the temporal change rate of the Stokes vector.

Therefore, in the prior-art method in which probing of vibration or the like is performed on the basis of a temporal change of the Stokes vector as disclosed in Patent Literatures 1 and 2, it is likely that overlooking or false notification of vibration can occur.

On the other hand, as described above by referring to FIG. 3, the rotation matrix R(t) expressing birefringence of the loop-state optical fiber 107 is equal not depending on clockwise or counterclockwise, and a temporal change of an absolute value of the angular velocity vector $\omega_b$ acquired from the rotation matrix R(t) is equal in principle regardless of whether it is clockwise or counterclockwise. Thus, the start time of the temporal change of the absolute value of this angular velocity vector $\omega_b$ to the respective light waves propagating clockwise and counterclockwise through the loop-state optical fiber 107 to be output can be strictly compared, and the birefringence fluctuation position can be acquired with accuracy from the time difference.

That is, according to the optical fiber sensor device according to the embodiment of the present invention and the vibration position specifying method using this device, since a measurement target is the temporal change of the angular velocity vector indicating birefringence specific to the optical fiber, probing of vibration or the like is executed without depending on the polarization state of the input light wave.

Heretofore, preferred embodiments of the present invention have been described in detail with reference to the appended drawings, but the present invention is not limited thereto. It should be understood that they will naturally come under the technical scope of the present invention.

What is claimed is:
1. An optical fiber sensor device comprising:
a probe light supply unit, an optical fiber sensor unit, and a polarization state measuring unit, wherein
the probe light supply unit generates and outputs a polarization switched light beam by alternately switching a polarized continuous wave light beam in polarization directions orthogonal to each other with elapse of time, the optical fiber sensor unit includes a loop-state optical fiber into which the polarization switched light beam is input and which outputs a light wave reflecting a change of birefringence according to a stress applied from an outside in the polarization switched light beam, and the polarization state measuring unit observes polarization states of the respective light waves propagating clockwise and counterclockwise through the loop-state optical fiber to be output, and calculates an angular velocity vector $\omega_b$ defined by an equation (1) that specifies a relationship between a temporal change rate $ds_{out}(t)/dt$ of a Stokes vector $s_{out}(t)$ giving a polarization state of the light wave output from the loop-state optical fiber and the Stokes vector $s_{out}(t)$ for each of the clockwise and counterclockwise light waves, the angular velocity vector $\omega_b$ giving a direction of a rotation center axis and a rotation angular velocity of the Stokes vector $s_{out}(t)$.

$$\frac{d}{dt}\vec{s}_{out}(t) = \vec{\omega}_b \times \vec{s}_{out}(t). \tag{1}$$

2. The optical fiber sensor device according to claim 1, wherein
the polarization state measuring unit specifies a fluctuation position of birefringence of the optical fiber from a difference in start time of a temporal change of an absolute value of the angular velocity vector $\omega_b$ with respect to each of the light waves propagating clockwise and counterclockwise through the loop-state optical fiber to be output.

3. The optical fiber sensor device according to claim 1, wherein
assuming that the angular velocity vector $\omega_b$ is $(\omega_{b1}, \omega_{b2}, \omega_{b3})^T$, an angular velocity vector product operator expression "$\omega_b \times$" is given by an equation (2).

$$\vec{\omega}_b \times = \begin{bmatrix} 0 & -\omega_{b3} & \omega_{b2} \\ \omega_{b3} & 0 & -\omega_{b1} \\ -\omega_{b2} & \omega_{b1} & 0 \end{bmatrix}. \tag{2}$$

4. The optical fiber sensor device according to claim 1, wherein
the probe light supply unit includes a laser light source, a polarization switch, a rectangular wave generator, and an optical branching device,
the optical fiber sensor unit includes a first optical circulator, a second optical circulator, and the loop-state optical fiber,
the polarization state measuring unit includes a first polarimeter, a second polarimeter, an analog-digital converter, and an angular velocity vector calculator,
the laser light source outputs the continuous wave light beam, and the rectangular wave generator supplies a rectangular wave electric signal to the polarization switch,
the polarization switch generates and outputs the polarization switched light beam by alternately switching the continuous wave light beam in synchronization with the rectangular wave electric signal in polarization directions orthogonal to each other with elapse of time, the optical branching device branches the polarization switched light beam into two parts and supplies the two parts to the first optical circulator and the second optical circulator, one of the polarization switched light beams having been branched into two parts is input through the first optical circulator into the loop-state optical fiber so as to propagate clockwise, while the other is input through the second optical circulator into the loop-state optical fiber so as to propagate counterclockwise, and the polarization switched light beam propagating clockwise through the loop-state optical fiber to be output from the loop-state optical fiber is input into the second polarimeter through the second optical circulator and thereby a Stokes parameter of the polarization switched light beam is observed by the second polarimeter, the polarization switched light beam propagating counterclockwise through the loop-state optical fiber to be output from the loop-state optical fiber is input into the first polarimeter through the first optical circulator and thereby a Stokes parameter of the polarization switched light beam is observed by the first polarimeter, the Stokes parameters observed by the first and second polarimeters are converted into digital signals by the analog-digital converter to be input into the angular velocity vector calculator, and the angular velocity vector calculator calculates the angular velocity vector $\omega_b$ from the Stokes parameters observed by the first and second polarimeters.

5. A vibration position specifying method, comprising:
generating and outputting a polarization switched light beam by alternately switching a polarized continuous wave light beam in polarization directions orthogonal to each other with elapse of time;
branching the polarization switched light beam into two parts and observing polarization states of respective light waves propagating clockwise and counterclockwise through a loop-state optical fiber to be output from the loop-state optical fiber; and
calculating an angular velocity vector $\omega_b$ defined by an equation (3) that specifies a relationship between a temporal change rate $ds_{out}(t)/dt$ of a Stokes vector $s_{out}(t)$ giving a polarization state of each of the light waves output from the optical fiber and the Stokes vector $s_{out}(t)$, the angular velocity vector $\omega_b$ giving a direction of a rotation center axis and a rotation angular velocity of the Stokes vector $s_{out}(t)$.

$$\frac{d}{dt}\vec{s}_{out}(t) = \vec{\omega}_b \times \vec{s}_{out}(t). \tag{3}$$

6. The vibration position specifying method according to claim 5, further comprising:
specifying a fluctuation position of birefringence of the optical fiber from a difference in start time of a temporal change of an absolute value of the angular velocity vector $\omega_b$ with respect to each of the light waves propagating clockwise and counterclockwise through the loop-state optical fiber to be output.

7. The vibration position specifying method according to claim 5, wherein
in calculation of the angular velocity vector, assuming that the angular velocity vector $\omega_b$ is $(\omega_{b1}, \omega_{b2}, \omega_{b3})^T$, an angular velocity vector product operator expression "$\omega_b \times$" is given by an equation (4)

$$\vec{\omega}_b \times = \begin{bmatrix} 0 & -\omega_{b3} & \omega_{b2} \\ \omega_{b3} & 0 & -\omega_{b1} \\ -\omega_{b2} & \omega_{b1} & 0 \end{bmatrix}. \quad (4)$$

\* \* \* \* \*